United States Patent [19]

Drent

[11] Patent Number: 4,691,047
[45] Date of Patent: Sep. 1, 1987

[54] PREPARATION OF CARBOXYLIC DI-ESTERS OR ACIDS

[75] Inventor: Eit Drent, Amsterdam, Netherlands

[73] Assignee: Shell Oil Company, Houston, Tex.

[21] Appl. No.: 844,429

[22] Filed: Mar. 26, 1986

[30] Foreign Application Priority Data

Apr. 15, 1985 [GB] United Kingdom ............... 8509641

[51] Int. Cl.[4] ...................... C07C 67/38; C07C 51/14
[52] U.S. Cl. .................................... 560/204; 502/155;
560/81; 560/97; 560/121; 560/123; 560/127;
560/193; 562/489; 562/497; 562/503; 562/505;
562/506; 562/509; 562/590
[58] Field of Search ................... 560/86, 97, 121, 123,
560/124, 127, 193, 204; 562/489, 503, 505, 497,
506, 509, 590; 502/155

[56] References Cited

U.S. PATENT DOCUMENTS

3,437,676  4/1969  Kutepow et al. .................. 560/114
3,501,518  3/1970  Kutepow et al. .................. 560/114

FOREIGN PATENT DOCUMENTS

0106379  4/1984  European Pat. Off. .
1110405  4/1986  United Kingdom .

*Primary Examiner*—Werren B. Lone
*Assistant Examiner*—Vera C. Clarke

[57] ABSTRACT

A process for the carbonylation of a conjugated diene with CO and an alcohol or water in the presence of an aprotic solvent is carried out in the presence of a dissolved catalytic system prepared by combining a Pd(II) compound, at least 5 mol of a triarylphosphine per gram atom of Pd and at least 1 mol of HCl per gram atom of trivalent P.

14 Claims, No Drawings

PREPARATION OF CARBOXYLIC DI-ESTERS OR ACIDS

FIELD OF THE INVENTION

The invention relates to a process for the production of carboxylic di-esters or dicarboxylic acids.

BACKGROUND OF THE INVENTION

It is known that olefinically unsaturated compounds having two conjugated carbon-carbon double bonds can be catalytically carbonylated with carbon monoxide and an alcohol to yield carboxylic esters. However, the known processes have various drawbacks which render them rather unattractive for use on a commercial scale.

A process for the preparation of carboxylic esters or carboxylic acids by reacting 1,3-butadiene with carbon monoxide and an alcohol or water and in the presence of a palladium catalyst is described in U.S. Pat. No. 3,501,518. The palladium catalyst is prepared by combining (a) palladium metal or a palladium chalcogenide, (b) an organic phosphine, for example a triarylphosphine and (c) an acid, for example hydrogen chloride. The palladium metal or palladium chalcogenide is present as a solid phase dispersed in the reaction mixture. Example 15 of the patent shows that a very high pressure of carbon monoxide was used and that, starting from 1,3-butadiene, no carboxylic di-esters had been formed.

According to U.S. Pat. No. 3,437,676 1,3-butadiene can be reacted with carbon monoxide and an alcohol or water in the presence of a palladium catalyst having the formula $L_mPdX_n$, in which L may be an organic phosphine, X may be chloride, m is an integer from 1 to 4, n is 1 or 2 and m+n is 2 to 6. However, the pressures applied are very high: 709 bar in the two examples concerning the carbonylation of 1,3-butadiene. Moreover, carbonylation of both double bonds has not been observed: in Example 63 of the patent, the reaction mixture contained a monocarboxylic acid as the sole reaction product.

British Patent Specification No. 1,110,405 describes a process for the preparation of carboxylic esters by reacting a conjugated diene with carbon monoxide and an alcohol in the presence of a catalyst comprising palladium, an organic phosphine and halide ions. It is preferred slightly to acidify the reaction mixture, for example, by providing for the presence of toluenesulfonic acid therein. According to Example 3 of the specification, 1,3-butadiene is converted into a mixture of methyl 3-pentenoate, dimethyl 2-methylglutarate and dimethyl ethylsuccinate in the presence of diiodobis(tributylphosphine)palladium(II) and p-toluenesulfonic acid, but this conversion was carried out at the very high pressure of 1013 bar.

European Patent Application No. 0106379 describes a process for the carbonylation of an olefinically unsaturated compound with carbon monoxide in the presence of water, an alcohol and/or a caboxylic acid, a palladium catalyst, at least 5 mol of a phosphine $PR^1R^2R^3$ in which $R^1$, $R^2$ and $R^3$ each represent an optionally substituted aryl group, per gram atom of palladium and an acid with a $pK_a$ of less than 2, except hydrohalogenic and carboxylic acids. The Applicant has found that an olefinically unsaturated compound having two conjugated carbon-carbon double bonds is hardly converted, if at all, with this known process.

It has now been found that in the carbonylation of olefinically unsaturated compounds having two conjugated carbon-carbon double bonds high yields of carboxylic di-esters can be obtained at a relatively low partial pressure of carbon monoxide by carrying out the reaction in the presence of a catalytic system defined more closely hereinafter.

SUMMARY OF THE INVENTION

The invention relates to a process for the production of carboxylic di-esters or dicarboxylic acids, which process comprises reacting an olefinically unsaturated compound having two conjugated carbon-carbon double bonds with carbon monoxide and with an alcohol or water in the presence of an aprotic solvent and a dissolved catalytic system prepared by combining:

(a) a divalent palladium compound, (b) an organic phosphine of the general formula

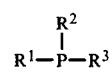

in which $R^1$, $R^2$ and $R^3$ each individually represent an aryl group, optionally substituted with one or more electron-withdrawing substituents, at least 5 gram atom of trivalent phosphorus per gram atom of divalent palladium being present in the catalytic system, and (c) at least one mol of hydrogen chloride per atom of trivalent phosphorus present in the catalytic system.

DESCRIPTION OF THE PREFERRED EMBODIMENTS

The olefinically unsaturated compound having two conjugated carbon-carbon double bonds may be an unsubstituted or a substituted alkadiene or cycloalkadiene, preferably having 4 to 30 and in particular 4 to 20 carbon atoms per molecule. The alkadiene or cycloalkadiene may be substituted with, for instance, one or more halogen atoms or cyano, ester, alkoxy, carboxy or aryl groups. If the substituents are not inert under the reaction conditions, the carbonylation reaction may be accompanied with other reactions. Examples of suitable olefinically unsaturated compounds are 1,3-alkadienes, for example, 1,3-tetradecadiene and 1,3-hexadecadiene. Other examples are 1,3-butadienylcyclohexane, 5-chloro-1,3-pentadiene, 1,3-hexadiene, 6-chloro-1,3-hexadiene, 3,5-pentadienylbenzene and 4-(2,4-butadienyl)toluene. Very good results have been obtained with 1,3-butadiene, which is usually quantitatively converted with high selectivity to carboxylic di-esters. The selectivity to a certain compound expressed in a percentage is defined as $$\frac{a}{b} \times 100$$

in which "a" is the amount of olefinically unsaturated compound that has been converted into that certain compound and "b" is the total amount of olefinically unsaturated compound that has been converted.

1,3-Butadiene is partly converted into dimethyl adipate, dimethyl 2-methylglutarate and dimethyl 2-ethylsuccinate. It is an advantage of the process according to the present invention that the carboxylic di-esters are formed in one step. Dimethyl adipate can easily be converted into adipic acid, which is a starting material in the manufacture of fibers or engineering plastics. Dimethyl 2-methylgutarate and dimethyl 2-ethylsuccinate can be used for the preparation of surface active ester mixtures (German Auslegeschrift No. 2,517,354) and pharmaceutical products (U.S. Pat. No. 4,105,789 and No. 4,154,937). Dimethyl 2-methylglutarate may be used for the preparation of flavor imparting agents (U.S. Pat. No. 4,168,280) and curing agents for epoxy resins (European Patent Application No. 88,047). The balance of the 1,3-butadiene is converted into methyl 3-pentenoate. This mono-ester can be isolated from the reaction mixture and subjected to a second carbonylation step for conversion into carboxylic di-esters.

Modifying the process according to the invention by replacing one, two or three aryl groups in the phosphine of the general formula I with an alkyl or a cycloalkyl group or by using one or more aryl groups carrying an electron-donating substituent, such as a p-alkoxy group (para with respect to the C-P bond) or a dialkylamino group results in a low conversion of the starting olefinically unsaturated compound and a low selectivity to carboxylic di-esters, if any. Each of the aryl groups $R^1$, $R^2$ and $R^3$ preferably contains not more than 18, in particular 6-14, carbon atoms. Examples of suitable $R^1$, $R^2$ and $R^3$ groups are the naphthyl group and, in particular, the phenyl group.

The presence of an electron-withdrawing substituent on the aryl groups $R^1$, $R^2$ and $R^3$ usually allows a higher selectivity to carboxylic di-esters. Examples of electron-withdrawing substituents are chlorine and fluorine atoms and nitro, trihalomethyl, m-alkoxy and m-aryloxy groups (meta with respect to the C-P bond) and "halo" representing iodo, bromo, chloro or fluoro. Good results have been obtained with trifluoro groups. Other examples are monohalomethyl and dihalomethyl groups.

According to a preferred embodiment of the present invention, a considerably enhanced selectivity to carboxylic di-esters in which the two carbonyl groups are located in a 1,4-position, with the same conversion of the starting olefinically unsaturated compound, is obtained when an organic phosphine of the general formula

is also combined with the catalytic system. In formula II $R^4$, $R^5$, $R^6$ and $R^7$ each individually representing an aryl group, optionally substituted with one or more electron-withdrawing substituents, and Q representing an alkylene group having 1 to 6 carbon atoms in a straight chain between the two phosphorus atoms. In this manner, 1,3-butadiene can be converted with enhanced selectivity into dimethyl adipate. This effect is very surprising, because the presence of an organic phosphine of the general formula II as the sole organic phosphine results in very little, if any carbonylation. Preferably, $R^4$, $R^5$, $R^6$ and $R^7$ are equal and, in particular, represent phenyl groups. The alkylene group Q preferably has 2 to 6 carbon atoms in the said straight chain and, more preferably, consists of 2 to 6 methylene groups. Very good results have been obtained with 1,4-di(diphenylphosphino)butane.

It was found that when the present process is modified by using less than 5 gram atom of trivalent phosphorus (if a phosphine of formula II is also present, calculated on the sum of the phosphines of formula I and II) per gram atom of palladium, the conversion of the starting olefinically unsaturated compound is low with a high selectivity to carboxylic mono-esters. Suitably, not more than 150 and usually not more than 50 gram atom of trivalent phosphorus are used per gram atom of divalent palladium.

It was also found that replacing the hydrogen chloride with
(a) hydrogen fluoride did not lead to any conversion of the starting olefinically unsaturated compound at all,
(b) hydrogen iodide or p-toluenesulphonic acid gave an extremely low conversion of the starting olefinically unsaturated compound,
(c) hydrogen bromide gave a low conversion of the starting compound.

Modifying the present process by using less than one mol of the hydrogen chloride per atom of trivalent phosphorus present in the catalytic system gives reduced formation of carboxylic di-esters. Preferably, not more than 10 mol of hydrogen chloride are used per gram atom of trivalent phosphorus present in the catalytic system, but this ratio may be higher than 10, for example up to 50, if desired.

The alcohols used in the process according to the invention may be aliphatic, cycloaliphatic or aromatic and may be substituted with one or more substituents, such as mentioned hereinbefore in connection with the olefinically unsaturated compounds to be used as starting material. The alcohol may therefore also be a phenol. The alcohols preferably contain not more than 20 carbon atoms per molecule. Examples of suitable alcohols are methanol, ethanol, propanol, 2-propanol, butanol, isobutanol, tert-butyl alcohol, 2-ethylhexanol, n-decanol, stearyl alcohol, benzyl alcohol, cyclohexanol, allyl alcohol, chlorocapryl alcohol, ethylene glycol, 1,2-propanediol, 1,4-butanediol, glycerol, polyethylene glycol, 1,6-hexanediol, phenol, the cresols and the xylenols. Special preference is given to alkanols having 1 to 10 carbon atoms per molecule. Very good results have been obtained with methanol. If the alcohol has more than one hydroxy group per molecule, different carboxylic di-esters may be formed, depending on the molar ratio existing between the reagents. For instance, depending on the quantity of olefinically unsaturated compound used, either a glycerol mono-ester or a glycerol di-ester may be produced from glycerol. The presence of water in the reaction mixture allows formation of dicarboxylic acids. Mixtures of an alcohol and water may be used, in which case a mixture of caboxylic di-esters and dicarboxylic acids is formed.

Suitable divalent palladium compounds are the salts of palladium with, for instance, hydrogen chloride, nitric acid, sulfuric acid or alkanoic acids having not more than 12 carbon atoms per molecule. A catalyst used by preference is palladium acetate. Palladium complexes may be used, for example, palladium acetylacetonate or bis-triphenylphosphinepalladium sulfate.

The quantity of palladium catalyst is not critical. Preference is given to the use of quantities in the range between $10^{-5}$ and $10^{-1}$ gram atom palladium per mol of olefinically unsaturated compound.

In the process according to the invention, the carbon monoxide may be used pure or diluted with an inert gas, such as nitrogen, noble gases or carbon dioxide. Generally, the presence of more than 10% by volume of hydrogen is undesirable, since under the reaction conditions it may cause hydrogenation of the olefinic compound. Generally, preference is given to the use of carbon monoxide or a carbon monoxide-containing gas which contains less than 5% by volume of hydrogen.

The present process is preferably carried out at a temperature in the range between 50° C. and 200° C. The total pressure preferably lies between 1 and 100, in particular 20 and 75 bar.

The molar ratio of the olefinically unsaturated compound to the alcohol is not critical. The molar ratio between hydroxy groups and olefinic double bonds may lie, for instance, between 0.1:1 and 10:1; preference is given to the use of the minimum amount of one equivalent for each carbon-carbon double bond.

The process according to the present invention is carried out in the presence of an aprotic solvent. It has been found that replacing the aprotic solvent with a protic solvent, such as, for example, methanol, gives very little conversion of the starting olefinically unsaturated compound. Good results have been obtained with ethers, in particular with anisole, 2,5,8-trioxanonane (also referred to as "diglyme") and diphenyl ether. Another example of a suitable ether is diisopropyl ether. Good results have also been obtained with aromatic hydrocarbons, in particular with toluene; other examples are benzene and the xylenes. Further examples of suitable aprotic solvents are sulfoxides, such as, for example, dimethyl sulfoxide, and sulfones such as, for example, diisopropyl sulfone and tetrahydrothiophene 1,1-dioxide (also referred to as "sulfolane"). A reaction product of the carbonylation reaction may also be used as a solvent.

The process according to the invention may be carried out batchwise, continuously or semi-continuously.

The invention is further illustrated by means of the following Examples which are not to be construed as limiting the invention.

EXAMPLES

Examples 1-12 and Comparative Experiments A–K were carried out in the following manner. A 250-ml magnetically stirred Hastelloy C autoclave ("Hastelloy" is a trade mark) was charged with methanol (10 ml) and a solvent (40 ml). 1,3-butadiene was conducted through the liquid until the volume was increased by 10 ml. Subsequently, palladium acetate (1 mmol), a phosphine and an acid were added. The Table hereinafter states which solvent, phosphine and acid were used and the quantities of the phosphine and the acid. The autoclave was flushed with carbon monoxide, and pressurized with carbon monoxide till a partial pressure of the value given in the Table was reached, sealed and heated to the temperature stated in the Table. After a reaction time of 5 hours, the contents of the autoclave were analyzed by means of gas-liquid chromatography. The conversion of 1,3-butadiene and the selectivities to methyl 3-pentenoate and to methyl esters of alkanoic acids having 6 carbon atoms per molecule are presented in the Table. This Table also presents the mol% of dimethyl adipate in the methyl esters of alkanoic acids having 6 carbon atoms per molecule.

Comparative Experiments A, B, C and E show that the presence of p-toluenesulfonic acid, hydrogen iodide and hydrogen fluoride does not lead to dicarbonylation.

Comparative Experiment D shows that the presence of hydrogen bromide leads to very little dicarbonylation.

Comparison of Example 1 where a molar ratio phosphine to palladium of 6 was used with Comparative Experiment F where this ratio was 3, shows more dicarbonylation in Example 1 with a higher fraction of dimethyl adipate.

Comparison of Example 2 where a molar ratio hydrogen chloride to phosphine of 2⅔ was used with Comparative Experiment G where this ratio was ⅔ shows more dicarbonylation in Example 2.

Examples 2, 3 and 4 show that diglyme, anisole and diphenyl ether respectively, are good solvents.

Comparative Experiment H shows no reaction in methanol as a solvent.

Comparative Experiment I shows no dicarbonylation in the presence of diethylphenylphosphine.

Comparative Example J shows no dicarbonylation in the presence of a phosphine having an electron-donating substituent on the phenyl groups.

Comparison of Examples 6 and 3 shows slightly more dicarbonylation and selectively to dimethyl adipate in the presence of anisole and a chlorine substituent on the phenyl group.

Comparison of Examples 7 and 4 shows more dicarbonylation in the presence of diphenyl ether and a chlorine substituent on the phenyl group.

Comparison of Examples 5 and 8 shows that the presence of a fluorine substituent on the phenyl group gives more dicarbonylation than the presence of a chlorine substituent.

Comparison of Examples 9 and 3 shows that the presence of a trifluoromethyl group gives more dicarbonylation with less formation of dimethyl adipate.

Comparison of Examples 10 and 11 shows that the presence of 1,4-di(diphenylphosphino)butane in combination with tri(m-methoxyphenyl)phosphine results in a considerably enhanced selectivity to dimethyl adipate. Example 12 shows that also very good results are obtained by combining the former phosphine with tri(m-chlorophenyl)phosphine.

Comparative Experiment K shows that no reaction takes place in the presence of 1,4-di(diphenylphosphino)butane as the sole phosphine.

EXAMPLE 13

Example 1 was modified by replacing the 1,3-butadiene with 1,3-cyclohexadiene (10 ml) and by using a temperature of 135° C. instead of 150° C. The conversion of 1,3-cyclohexadiene was 95% and the selectivities to cyclohexenemonocarboxylic acids and cyclohexanedicarboxylic acids were 26% and 74%, respectively.

TABLE

| Example | Comp. Exp. | Catalytic System | | | | Solvent | Temperature, °C. | Partial pressure CO, bar | Conversion butadiene, % | Selectivity, %, to | | |
|---|---|---|---|---|---|---|---|---|---|---|---|---|
| | | Phosphine | mmol | Acid | mmol | | | | | $A^3$ | $B^4$ | $C^5$ |
| 1 | | triphenyl-phosphine | 6 | HCl | 8 | toluene | 150 | 50 | 100 | 18 | 82 | 25 |
| | A | triphenyl- | 6 | p-toluene | 8 | " | 150 | 50 | trace | — | — | — |

TABLE-continued

| Example | Comp. Exp. | Catalytic System Phosphine | mmol | Acid | mmol | Solvent | Temperature, °C. | Partial pressure CO, bar | Conversion butadiene, % | Selectivity, %, to A[3] | B[4] | C[5] |
|---|---|---|---|---|---|---|---|---|---|---|---|---|
| | | phosphine | | sulphonic acid | | | | | | | | |
| | B | triphenyl-phosphine | 6 | HCl p-toluene sulphonic acid | 4 4 | " | 150 | 50 | 30 | 100 | 0 | — |
| | C | triphenyl-phosphine | 6 | HI | 8 | diglyme | 150 | 50 | 5 | 100 | 0 | — |
| | D | triphenyl-phosphine | 6 | HBr | 8 | toluene | 155 | 50 | 40 | 90 | 10 | not determined |
| | E | triphenyl-phosphine | 6 | HF | 8 | " | 150 | 50 | 0 | — | — | — |
| 2 | | triphenyl-phosphine | 6 | HCl | 16 | diglyme | 135 | 50 | 100 | 33 | 67 | 30 |
| | F | triphenyl-phosphine | 3 | HCl | 4 | toluene | 150 | 50 | 60 | 48 | 52 | 20 |
| | G | triphenyl-phosphine | 6 | HCl | 4 | diglyme | 155 | 50 | 80 | 75 | 25 | 20 |
| 3 | | triphenyl-phosphine | 6 | HCl | 8 | anisole | 155 | 50 | 100 | 22 | 78 | 28 |
| | H | triphenyl-phosphine | 6 | HCl | 8 | methanol | 150 | 50 | trace | — | — | — |
| 4 | | triphenyl-phosphine | 6 | HCl | 8 | diphenyl ether | 155 | 50[1] | 90 | 25 | 75 | 36 |
| | I | diethyl-phenylphosphine | 6 | HCl | 8 | toluene | 150 | 50 | 20 | 100 | 0 | — |
| | J | tri(p-methoxy-phenyl)phosphine | 6 | HCl | 8 | diglyme | 155 | 50 | 60 | 100 | 0 | — |
| 5 | | tri(p-chloro-phenyl)phosphine | 6 | HCl | 8 | " | 150 | 50 | 100 | 40 | 60 | 32 |
| 6 | | tri(p-chloro-phenyl)phosphine | 6 | HCl | 8 | anisole | 155 | 50 | 100 | 20 | 80 | 31 |
| 7 | | tri(p-chloro-phenyl(phosphine | 6 | HCL | 8 | diphenyl ether | 155 | 50[2] | 100 | 20 | 80 | 35 |
| 8 | | tri(p-fluoro-phenyl)phosphine | 6 | HCl | 8 | diglyme | 150 | 50 | 100 | 32 | 68 | 32 |
| 9 | | tri(m-trifluoromethyl-phenyl)phosphine | 6 | HCl | 8 | anisole | 155 | 50 | 100 | 17 | 83 | 22 |
| 10 | | tri(m-methoxy-phenyl)phosphine | 6 | HCl | 8 | diphenyl ether | 155 | 50[2] | 100 | 25 | 75 | 42 |
| 11 | | 1,4-di(di-phenylphosphino)-butane tri(m-methoxy-phenyl)phosphine | 2 8 | HCl | 16 | diphenyl ether | 155 | 60[2] | 100 | 25 | 75 | 53 |
| 12 | | 1,4-di(di-phenylphosphino)-butane tri(m-chloro-phenyl)phosphine | 5 2 | HCl | 16 | diphenyl ether | 155 | 60[1] | 100 | 30 | 70 | 57 |
| | K | 1,4-di(di-phenylphosphino)-butane | 4 | HCl | 10 | diphenyl ether | 155 | 50 | trace | — | — | — |

[1] after 2.5 h of reaction the total pressure was released to 40 bar
[2] after 2.0 h of reaction the total pressure was released to 40 bar
[3] A = methyl 3-pentenoate
[4] B = methyl esters of $C_6$—alkanedioic acids
[5] C = fraction of dimethyl adipate, mol %, in methyl esters of $C_6$—alkanedioic acids

I claim:

1. A process for the production of carboxylic diesters, dicarboxylic acids or mixtures thereof, which process comprises reacting at a temperature in the range of from 50° C. to 200° C. an olefinically unsaturated compound having two conjugated carbon-carbon double bonds with carbon monoxide and with an alcohol or water in the presence of an aprotic solvent and a dissolved catalytic system prepared by combining:
    (a) a divalent palladium compound,
    (b) an organic phosphine of the formula

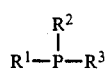

(I)

in which $R^1$, $R^2$ and $R^3$ each individually represent an aryl group, optionally substituted with one or more electron-with-drawing substituents, at least 5 gram atom of trivalent phosphorus per gram atom of divalent palladium being present in the catalytic system, and
    (c) at least one mol of hydrogen chloride per atom of trivalent phosphorus present in the catalytic system.

2. The process of claim 1 wherein the aryl groups represented by $R^1$, $R^2$ and $R^3$ are phenyl groups.

3. The process of claim 2 wherein the phenyl groups are substituted with a chlorine or fluorine atom or a trifluoromethyl or methoxy group, the methoxy groups on a meta position with respect to the C-P bonds.

4. The process of claim 1 wherein an organic phosphine of the formula

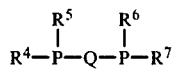
(II)

is combined with the catalytic system and wherein in formula II, $R^4$, $R^5$, $R^6$ and $R^7$ each individually represent an aryl group, optionally substituted with one or more electron-withdrawing substitutents, and Q represents an alkylene group having 1 to 6 carbon atoms in a straight chain between the two phosphorus atoms.

5. The process of claim 4 wherein $R^4$, $R^5$, $R^6$ and $R^7$ each represent a phenyl group.

6. The process of claim 4 wherein Q has 2 to 6 carbon atoms in the said straight chain.

7. The process of claim 6 wherein 1,4-di(diphenylphosphino)butane is combined with the catalytic system.

8. The process of claim 1 wherein not more than 150 gram atom of trivalent phosphorus are used per gram atom of divalent palladium.

9. The process of claim 1 wherein not more than 10 mol of hydrogen chloride are used per gram atom of trivalent phosphorus present in the catalytic system.

10. The process of claim 1 wherein it is carried out at a pressure of carbon monoxide in the range of from 10 to 100 bar.

11. The process of claim 1 wherein the olefinically unsaturated compound having two conjugated carbon-carbon double bonds is an alkadiene having up to 30 carbon atoms per molecule which can optionally be substituted with one or more halogen atoms or cyano, ester, alkoxy, carboxy or aryl groups.

12. The process of claim 11 wherein the olefinically unsaturated compound is 1,3-butadiene.

13. The process of claim 1 wherein the alcohol has not more than 20 carbon atoms per molecule.

14. The process of claim 13 wherein the alcohol is an alkanol having 1 to 10 carbon atoms per molecule.

* * * * *